United States Patent
Winthrop et al.

[11] Patent Number: 5,682,881
[45] Date of Patent: Nov. 4, 1997

[54] NASAL CPAP/CANNULA AND SECUREMENT APPARATUS

[76] Inventors: Neil Winthrop, 12A Amherst Ct., Royal Palm Beach, Fla. 33411; Harry Bayron, 7439 Pioneer Rd., West Palm Beach, Fla. 33413

[21] Appl. No.: 734,753

[22] Filed: Oct. 21, 1996

[51] Int. Cl.$^6$ .................................................. A61M 15/08
[52] U.S. Cl. ...................... 128/207.18; 128/204.23; 128/200.26; 128/911; 128/DIG. 26
[58] Field of Search .................. 128/207.18, 204.23, 128/911, 912, DIG. 26, 206.11, 200.26; 604/94, 178

[56] References Cited

U.S. PATENT DOCUMENTS

| | | |
|---|---|---|
| 3,513,844 | 5/1970 | Smith . |
| 4,106,505 | 8/1978 | Salter et al. . |
| 4,142,527 | 3/1979 | Garcia .............................. 128/DIG. 26 |
| 4,818,320 | 4/1989 | Weichselbaum .................... 128/207.18 |
| 4,823,789 | 4/1989 | Beisang . |
| 5,074,299 | 12/1991 | Dietz ................................ 128/204.23 |
| 5,135,506 | 8/1992 | Gentelia et al. .................. 128/DIG. 26 |
| 5,156,641 | 10/1992 | White . |
| 5,245,995 | 9/1993 | Sullivan et al. .................... 128/204.23 |
| 5,271,391 | 12/1993 | Graves . |
| 5,316,009 | 5/1994 | Yamada .............................. 128/204.23 |
| 5,335,656 | 8/1994 | Bowe et al. ........................ 128/207.18 |
| 5,477,852 | 12/1995 | Landis . |
| 5,495,848 | 3/1996 | Aylsworth et al. ................. 128/204.23 |
| 5,513,631 | 5/1996 | McWilliams ........................ 128/204.23 |
| 5,513,635 | 5/1996 | Bedi . |
| 5,533,506 | 7/1996 | Wood .................................. 128/200.26 |
| 5,540,219 | 7/1996 | Mechlenburg et al. ............. 128/204.23 |

*Primary Examiner*—Vincent Millin
*Assistant Examiner*—William J. Deane, Jr.
*Attorney, Agent, or Firm*—McHale & Slavin, PA

[57] ABSTRACT

A nasal continuous positive airway pressure (CPAP) and nasal cannula device, e.g. NCC device, with modular components and a mean airway pressure (MAP) measurement port. The NCC device includes a comfortable foam securement strip which adhesively attaches to the upper lip of an individual. The securement strip includes adhesive tape strips extending therefrom with removable backings for attaching the NCC device to the individual's face with the nasal prongs sealably positioned in the nose. The MAP measurement port can be located near the nasal prongs for accurate pressure readings or further away for convenience in reading the pressure. Extensions or tapping fixtures can also be used to provide a MAP measurement port at a convenient location away from the face. The NCC device could be used with modular connections including, for instance, ventilator circuit attachments and/or cannula flowmeter attachments.

18 Claims, 4 Drawing Sheets

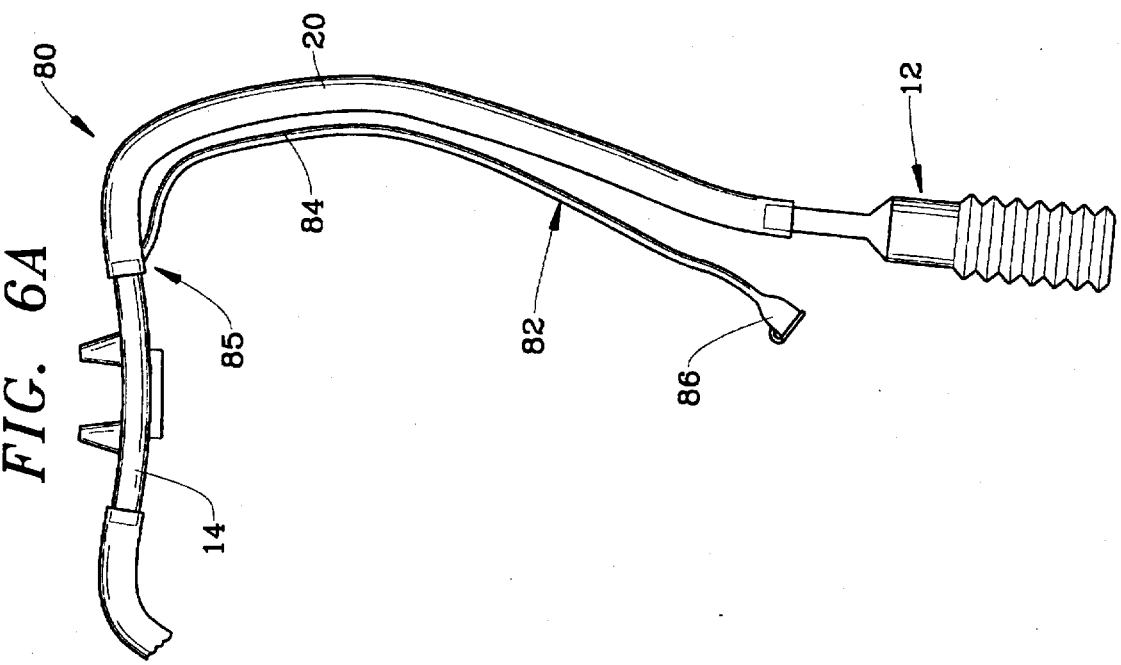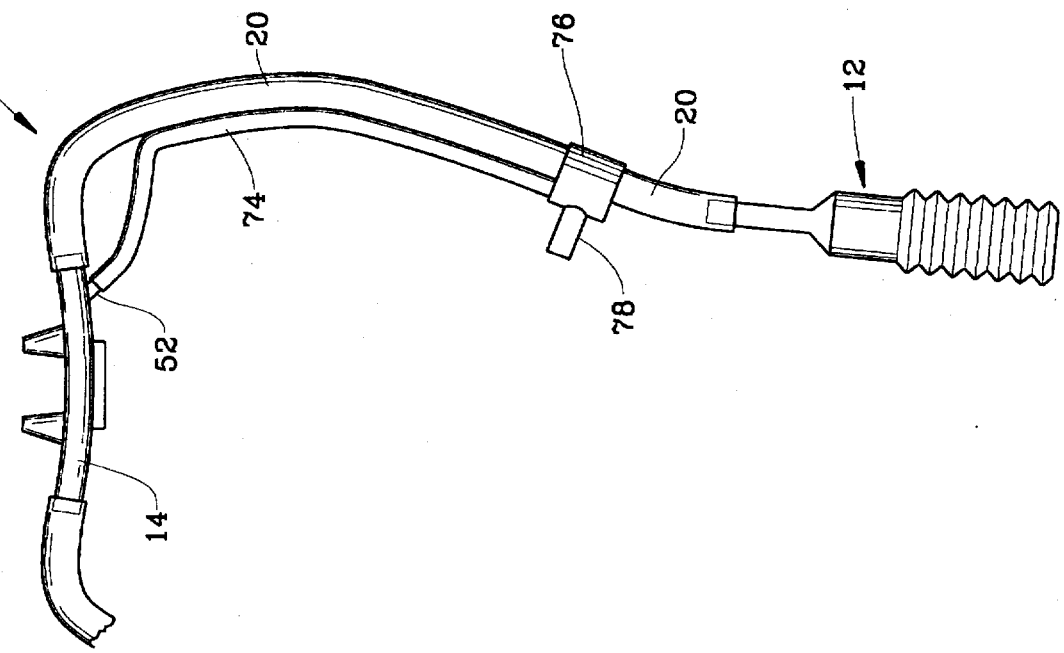

NASAL CPAP/CANNULA AND SECUREMENT APPARATUS

FIELD OF INVENTION

This invention relates generally to a nasal CPAP/cannula device with a comfortable securement strip for positioning the device in an individual's nares as the securement device is positioned under the nose. The cannula is designed as a comfortable CPAP device which requires less pressure to hold it in place. The device also converts to a high flow nasal cannula.

BACKGROUND OF THE INVENTION

Certain individuals require a respiratory supplement such as air, oxygen, or other gases. Such gases are freely supplied and/or supplied at controlled pressures. Such gases are also supplied through the patient's mouth and/or through the patient's nose. Nasal supply systems provide an advantage in that they are generally more convenient and less intrusive than mouth based or mouth covering devices. Despite their convenience, nasal based devices are deemed uncomfortable in light of securement straps placed across the face and/or around the head and used to secure the device to an individuals breathing cavity. Moreover, conventional cannulas do not provide a proper seal around the nares to inhibit apnea and to provide a high flow system to stimulate the patient's breathing. Hence, even with such securement straps, these nasal devices often dislodge from the breathing cavity. This is of particular concern with children, infants, or the elderly who do not understand the importance of keeping the nasal breathing device in place, whether it be a nasal CPAP or nasal cannula.

It is known to be beneficial and therapeutic to supply an individual with a sufficient amount of respiratory airway pressure in order to maintain a minimum level of air volume in the lungs. If the air volume falls below this minimum level, then the lungs may collapse, which can be extremely dangerous or even deadly to the individual. Moreover, the backpressure can increase oxygen levels in the lungs and decrease carbon dioxide levels. This will also improve PH by removal of carbon dioxide, which is an acid, from the blood. Hence, the application of such sufficient pressure, called continuous positive airway pressure (CPAP), has been found to be advantageous in maintaining a minimum air volume or lung pressure when an individual is spontaneously breathing. CPAP can be supplied through nasal attachment devices such as a nasal cannula, or through mouth based or endotracheal devices.

A number of CPAP devices are known including endotracheal tubes, head chambers, face chambers, face masks, nasal prongs, and nasal cannulas. While each type of device has advantages and disadvantages, the nasal cannula provides a comfortable alternative for providing CPAP and/or airflow assistance. Prior art nasal cannulas have been disclosed in many forms with various methods of securing the device to the nasal passageway. One such cannula assembly is disclosed in U.S. Pat. No. 3,513,844 which uses an adjustable strap that encircles an individual's head. A similar device is disclosed in U.S. Pat. No. 4,106,505 wherein the supply tubes to the cannula are hooked over an individual's ears and around the head. Even more cumbersome, U.S. Pat. No. 5,477,852 discloses a device with a headband for holding and positioning the nasal inserts and associated supply tubes. Yet another system in U.S. Pat. No. 5,271,391 discloses a cannula which is secured by applying strips of pressure sensitive adhesive tape to the supply tubes leading from each side of the cannula, thereby attaching the supply tubes to the cheeks of an individual with the cannula positioned in between.

Such "bonnet" type devices are commonly used to hold the CPAP prongs in place. However, this method generally puts pressure on an individual's nose and upper lip thereby causing pressure necrosis in the center of the nose. A particularly sensitive individual is a young child, infant or baby. The bonnet also fails to adequately keep the nasal prongs in position, particularly with infants who move or roll around in their crib. In a hospital or care facility setting, it is not uncommon for an attendant to discover that the CPAP device has been disconnected from a patient's nose, which can lead to apnea, desaturations, bradycardia, or hypoxia which is dangerously low oxygen levels in the blood. In practice, the tubing for these bonnet type CPAP's is draped around both sides of the patient's cheek which means that the most comfortable lying down position is on the patient's back. Pressure on the patient's cheeks caused by the securement device can make other position's undercomfortable.

Other prior art anchoring systems include adhesive devices which attach directly to the nose. U.S. Pat. No. 4,823,789 discloses a nose tube anchoring strip which has an adhesive coated sheet shaped to fit over an individual's nose and an appendage for holding a nasal-gastric tube. A similar system is found in U.S. Pat. No. 5,156,641 which has an anchoring cord adhesively attached to an individual's nose at one end and attached to hold a naso-gastric catheter at the other end. U.S. Pat. No. 5,513,635 provides a securement device with a body engagement portion which adheres across the nose of an individual with cannula engaging portions extending down therefrom.

In each instance, the nasal CPAP/cannula securement devices are cumbersome or ineffective in their attachment of the cannula to the patient. Accordingly, what is needed in the field is a securement device having a comfortable securement apparatus and method and which eliminates placement of supply tubes which wrap around the head to secure the CPAP/cannula device. The securement device should be easy to use and still provide steadfast attachment of the nasal CPAP/cannula device in position directly under an individual's nose. The device might also provide a port for assessment of the mean airway pressure (MAP) in the device so that CPAP can more accurately be monitored or controlled.

SUMMARY OF THE INVENTION

The instant invention discloses a nasal CPAP and nasal cannula design with a unique securement device which comfortably and securely adheres to the lip of an individual. The securement device is a foam strip platform with three alternating tape attachment strips for holding the nasal CPAP/cannula (NCC) in position under the nose. The CPAP/cannula device utilizes separate inspiratory and expiratory tubing to allow the individual, often times an infant, to be placed in any position without laying on the tubing.

The securement device serves to stabilize the nasal prongs of the NCC directly to the upper lip of an individual via use of two strips of adhesive tape extending from the top of the foam strip, and a centered strip of adhesive tape extending from the bottom to position the prongs in the nares. The foam strip is shaped to generically conform to the upper lip of most individuals, and comes in different sizes. A liquid adhesive for the skin, such as MASTISOL, can be utilized to attach the foam strip to the upper lip which also can be used to protect the skin. The tape strips allow for custom positioning of the NCC device on the attached foam strip according to each individual's needs. Such custom positioning promotes comfort and prevents disconnections, either accidental or otherwise, of the NCC device. Additionally, the NCC device uses cone shaped prongs to allow for a comfortable, yet secure fit with very little pressure being applied by the securement device. The combination of cone shaped prongs and adjustable securement tape will facilitate creation of a secure seal about the nares of the individual which enhances the effectiveness of the NCC device.

To use the securement device, the adhesive portions on the upper tape strips are exposed and drawn downward over sides of the NCC device, on either side of the nasal prongs. The bottom strip of tape is exposed and drawn up around the center of the NCC device so as to gently position the nasal prongs inside the nostrils, or nares, of an individual. A center tab might extend from the central body of the NCC device for stabilization, opposite the nasal prongs, to aid in attachment and positioning of the device on the foam pad. The NCC device is modular in design with a high flow nasal cannula section, detachable supply tubes, and modular supply tube connectors for connecting the NCC device to different supply sources and/or monitoring devices.

This securement device might also be used to attach other respiratory or gastric treatment aids, besides the discussed NCC device, with the existing tape strips, or with repositioned tape strips as needed. Such other respiratory or gastric treatment aids might include, for example, nasal-gastric tubes, PH probes, oral-gastric tubes, oral suction tubes, gastric secretions tubes, and/or conventional nasal cannulas.

Accordingly, it is an object of the present invention to provide an NCC and securement device designed to be attached to the upper lip of an individual with minimal discomfort and maximum effectiveness.

It is still another object of the present invention to provide an NCC and securement device which provides an additional MAP measurement connector for monitoring and controlling CPAP.

It is a further object of the present invention to provide an NCC device which is modular in design so that it might be used in a variety of applications.

It is yet another object of the present invention to provide an NCC and securement device which provides a foam strip with tape tab extensions, with the foam strip being attached to an individual's lip and with the tape strips holding the NCC device to the foam strip beneath the nose.

It is still another object of the present invention to provide an NCC and securement device which allows for more versatile positioning of the supply tubes, while securely maintaining the NCC device under an individual's nose.

It is a further object of the present invention to provide an NCC and securement device which is well suited for comfortable use on small or sensitive patients such as small children or infants.

Other objects and advantages of this invention will become apparent from the following description taken in conjunction with the accompanying drawings wherein are set forth, by way of illustration and example, certain embodiments of this invention. The drawings constitute a part of this specification and include exemplary embodiments of the present invention and illustrate various objects and features thereof.

BRIEF DESCRIPTION OF THE DRAWINGS

FIG. 6 is an overhead view of the NCC device of the present invention which includes a further alternative MAP measurement connection.

FIG. 6A is an overhead view of the NCC device of the present invention which includes yet another alternative MAP measurement connection.

DETAILED DESCRIPTION OF THE PREFERRED EMBODIMENT

Although the invention will be described in terms of a specific embodiment, it will be readily apparent to those skilled in this art that various modifications, rearrangements and substitutions can be made without departing from the spirit of the invention. The scope of the invention is defined by the claims appended hereto.

Figure 1:
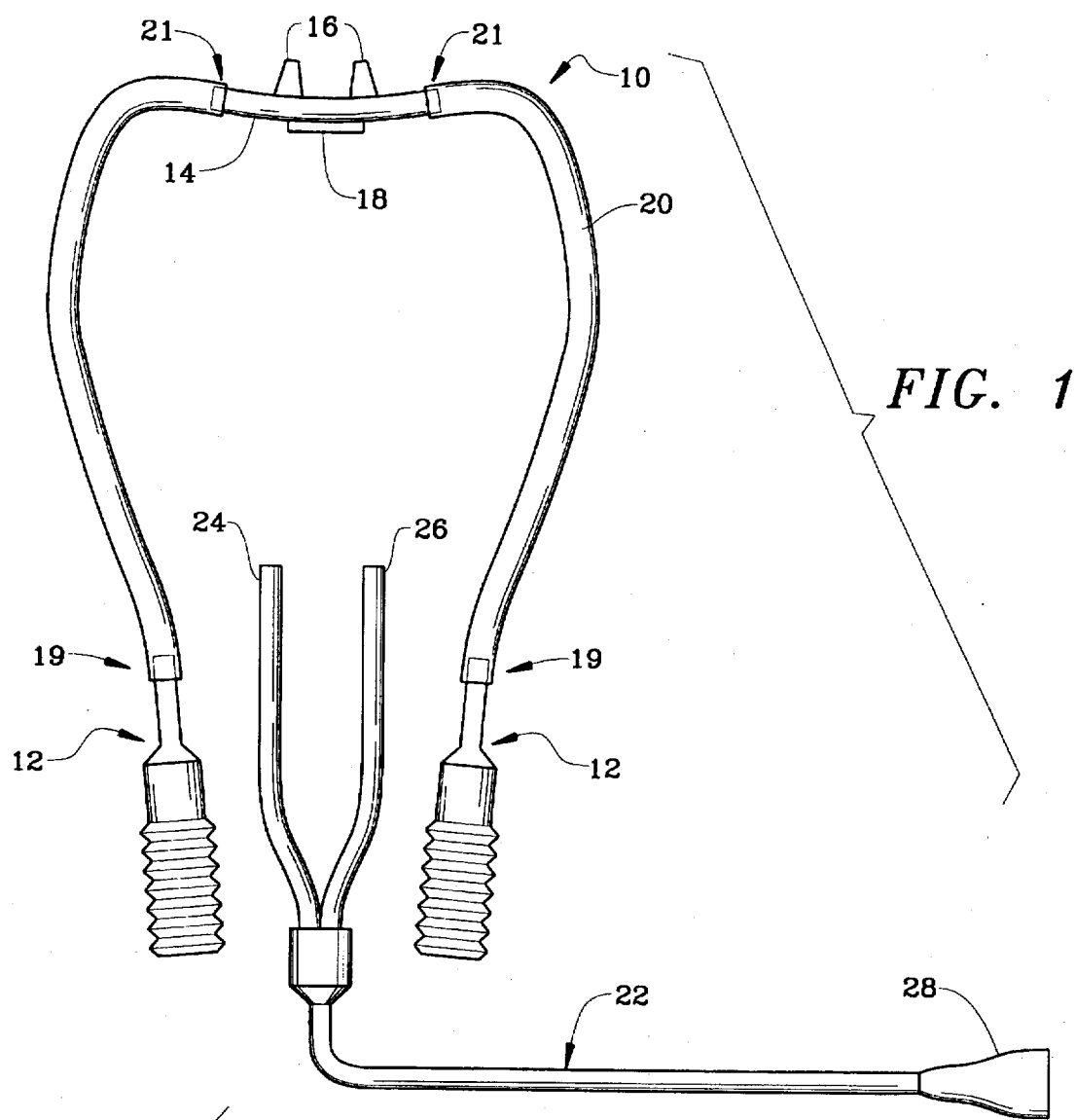
FIG. 1 is an overhead view of the modular NCC device of the present invention with ventilator circuit attachments, and alternative nasal cannula flow-meter attachments.

Referring now to FIG. 1, an NCC device 10 is shown with alternative modular connectors. The NCC device 10 includes a nasal prong section 14 with conically shaped nasal prongs 16. The cone shaped prongs 16 facilitate formation of a seal in the nares of the treated individual. A tab 18 is included opposite the prongs 16 to assist in attaching and positioning the prong section 14 to a securement device described later in this specification. A gas supply tube 20 extends from each side of the tubular prong section 14. The tube 20 is attached at its proximal end via a friction fit to the tubing 20 over each end 21 of section 14. Adhesive or sealant can be used to permanently attach or seal the tubing 20 to section 14. Alternatively, the tubing 20 could be integrally formed with section 14, thereby making section 14 and tubes 20 one continuous or cast part. The other end, or distal end, of the supply tubes 20 are modularly connected to ventilator circuit attachments 12 which frictionally fit into the ends 19 of the supply tubes 20. Alternatively, a Y-shaped nasal cannula flow-meter connector 22 might frictionally fit each Y-end 24 and 26 into the ends of the supply tubes 20. The Y-shaped tubes of the connector 22 join and end in a flow-meter connector 28 which is a nipple connector that attaches to the nipple of a flow meter. Again, the modular tube connections might be adhesively sealed or the device could be integrally formed throughout to directly include either such connector to produce this high flow nasal cannula. With such modular connections, a CPAP device, or a high flow nasal cannula, can be quickly configured according to the user's needs.

Figure 2:
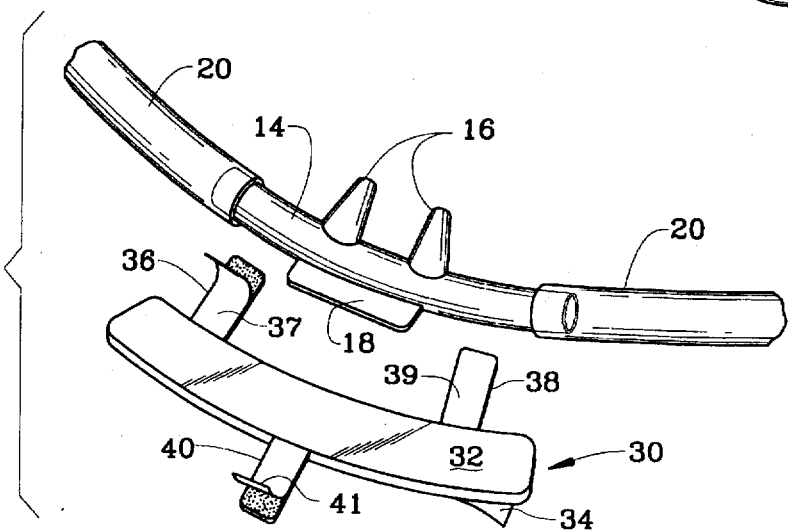
FIG. 2 is a perspective view of the nasal prong portion of the NCC device with the supply tubes extending therefrom and with the securement device being readied for attachment.

Referring now to FIG. 2, a perspective view of the nasal prong section 14 is shown attached to the supply tubes 20. The securement device 30 is shown positioned below and ready to attachably receive prong section 14. The securement device 30 includes a central foam strip 32 which is arcuate in shape. The foam strip 32 includes a low tack adhesive substance on its bottom side which is covered by a removable protective covering 34. The protective covering 34 can be peeled off in sections or as one piece. A liquid skin adhesive, such as MASTISOL, might also be applied to the patient's upper lip before attaching the foam strip 32. MASTISOL, or other such adhesives, might be used alone, or in conjunction with the adhesive backing, to achieve a secure and comfortable attachment to the lip. A pair of upper tape strips 36 and 38 extend from the top of the foam strip 32 and are positioned outside each nasal prong 16. A lower centered tape strip 40 extends from the bottom of the foam strip 32 and is positioned between the prongs 16. Tape strips 36, 38, and 40 include removable covering strips 37, 39, and 41 positioned over the adhesive portions of the tape. Tab 18 is also shown extending from the nasal prong section 14, with the tab 18 helping to flatly position and hold the prong section 14 to the foam strip 32 for placement beneath the nose.

Figure 3:
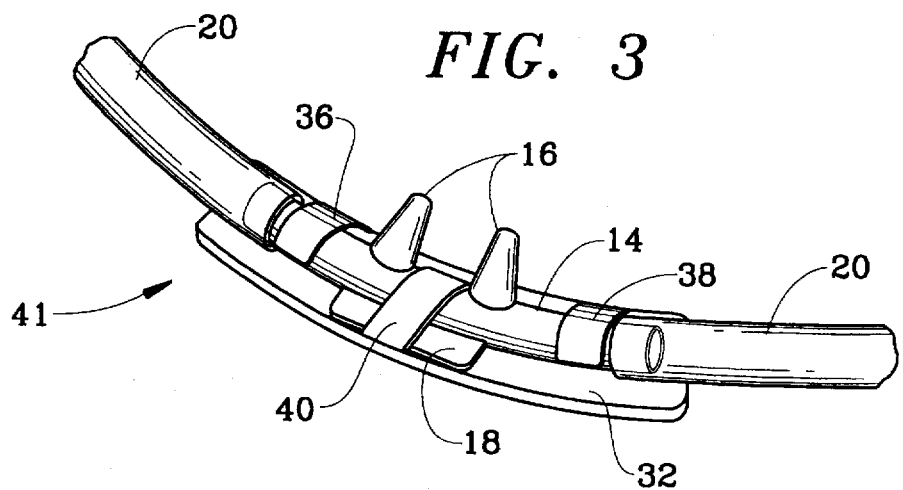
FIG. 3 is a perspective view of the nasal prong portion of FIG. 2 with the securement device attached.

Referring now to FIG. 3, a perspective view of the nasal prong section 14 and securement device 30 are shown operably attached together via the tapes strips 36, 38, and 40 to form a mounted NCC device 41. The peelable coverings 37, 39, and 41, shown in FIG. 2, have been removed. The prong section 14 is centrally positioned on the foam strip 32 with the prongs 16 facing upwards and the tab 18 facing downwards. The upper tape strips 36 and 38 are then wrapped down around and adhesively secured to the prong section 14 on either side of the nasal prongs 16. The lower tape strip 40 is wrapped upwards around section 14, over the positioning tab 18, and between the prongs 16. Tape strip 40 serves to provide upward adjustability or positioning of the NCC device to secure the cone shaped prongs 16 sealably against the individual's nose.

Figure 4:
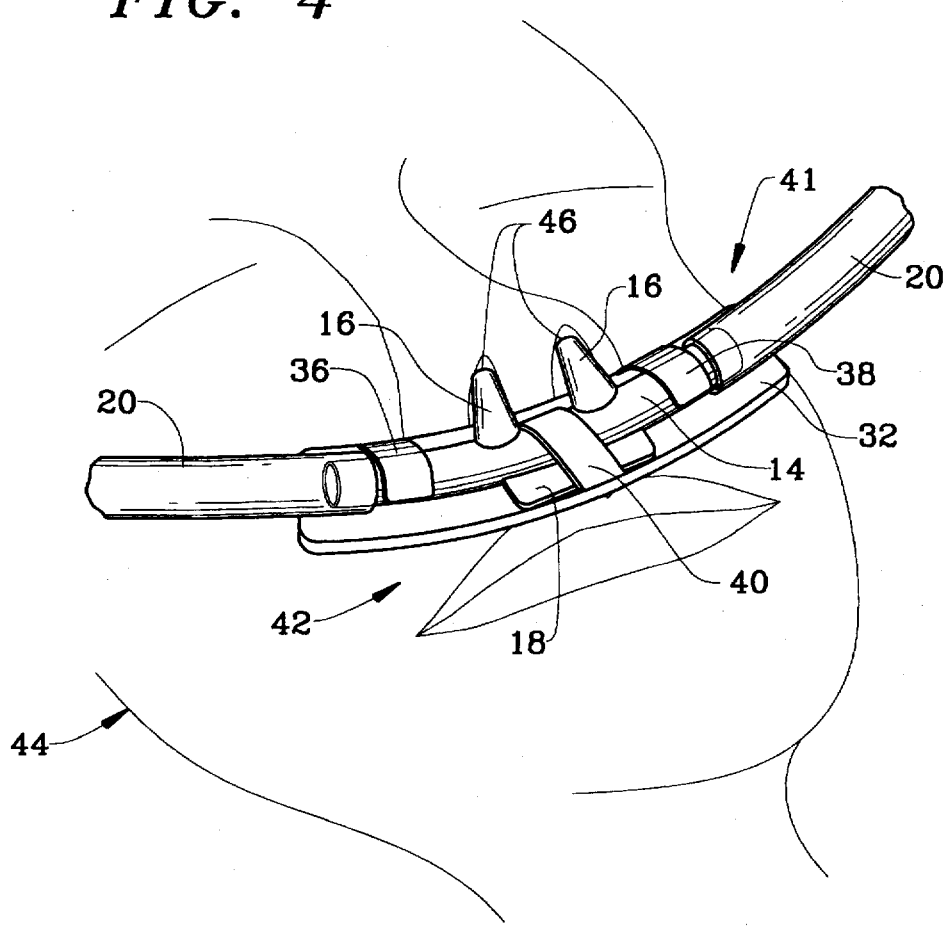
FIG. 4 is a perspective view of the NCC device and securement device of FIG. 3 attached to the upper lip of an individual.

Referring now to FIG. 4, the mounted NCC device 41 of FIG. 3 is shown attached to the upper lip 42 of an individual 44. The present invention facilitates two different methods of positioning the NCC device under the nose. In the first method, the foam strip 32 would first be mounted to the upper lip 42 via the described adhesives. Then, the nasal prong section 14 and attached supply tubes 20 are applied via the tape strips 36, 38, and 40. Tab 18 is again used to facilitate positioning the nasal prongs 16 in gentle, yet secure contact with the nares 46. In the second method, the mounted NCC device 41 is operably formed. Then, the foam strip 32 is adhesively mounted, as described above, to the upper lip 42 so that the nasal prongs 16 are correctly positioned in the nares 46 of the individual's nose.

Figure 5:
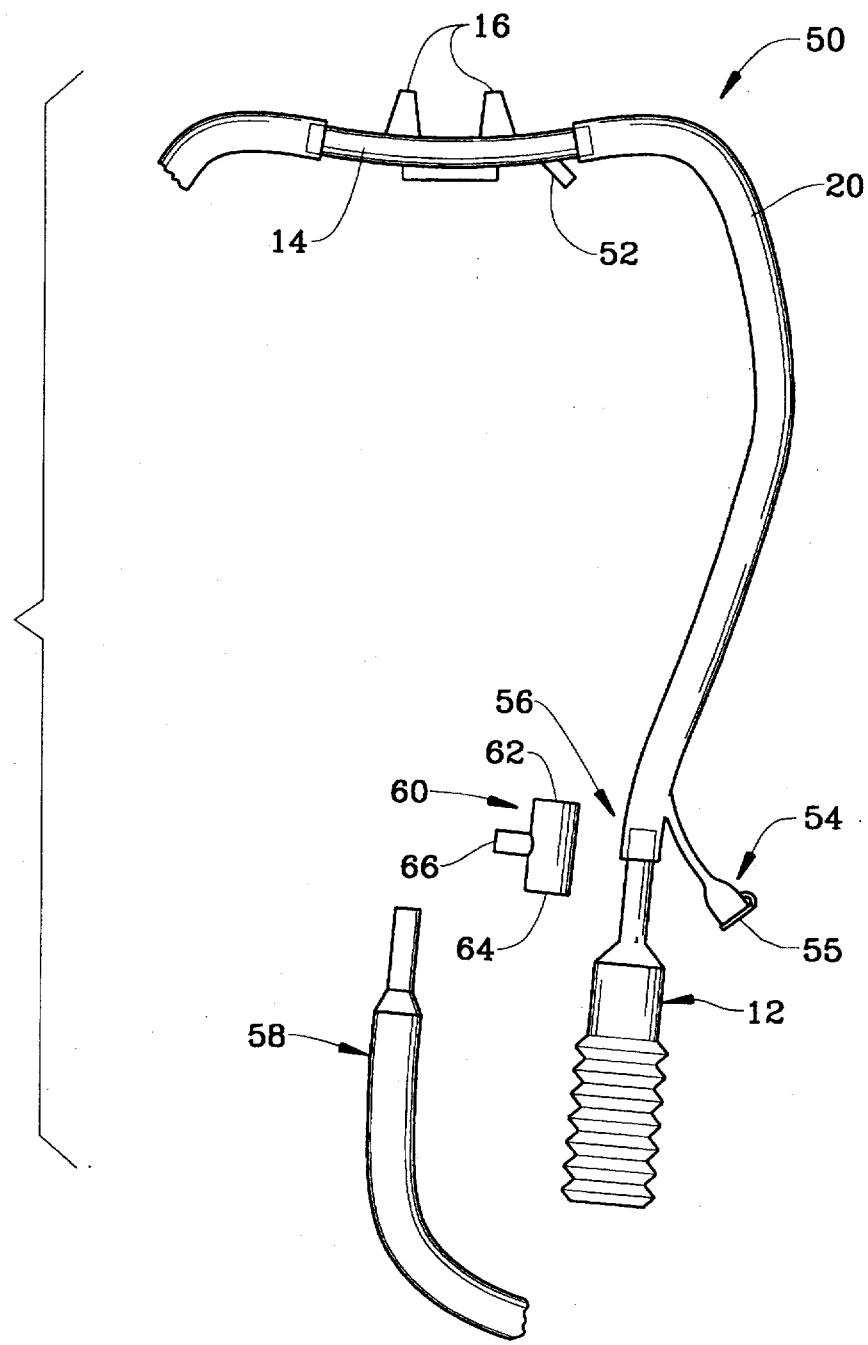
FIG. 5 is an overhead view of the NCC device of the present invention which includes a variety of alternative MAP measurement connectors.

Referring now to FIG. 5, an alternative embodiment 50 of the NCC device is shown, with one supply tube 20 shown and the other supply tube cutaway for convenience. In order to maintain the proper CPAP, it is important to have feedback from the air supply device as to the pressure supplied. Such pressure is often referred to as "mean airway pressure" or MAP. In this embodiment, a variety of MAP measurement connectors are shown. The nasal prong section 14 shows one possible MAP measurement connector 52 extending down from the bottom of section 14. This MAP connector location 52 is very close to the nasal prongs 16 and therefore will give a very accurate reading as to the pressure being supplied. A measurement tube 58 would be connected at 52 and would lead to a sensing device, not shown, which might help regulate the pressure supplied.

A MAP connector 54 might also branch out from the supply tube 20 near the distal end or modular end connection 56. As before, this supply tube end 56 can receive the ventilator circuit attachment 12, or the nasal cannula flow-meter connector 22 as shown in FIG. 1. The MAP connector 54 extends out from the supply tube 20 to facilitate convenient attachment of a measurement tube 58. When not in use, the connector is covered with tethered cap or plug 55.

Yet another embodiment uses a MAP connector formed from a T-shaped tubular fixture 60 which is frictionally or sealably fitted over the supply tube end 56 at a first end 62 of the T-shaped tube 60. The ventilator circuit attachment 12, or other connector 22 shown in FIG. 1, is fitted into the second end 64 of the T-shaped tube 60. The MAP measurement port 66 then extends perpendicularly from the side for attachment of the measurement tube 58.

These latter two MAP connection embodiments provide a pressure measurement which is further away from the nasal prongs 16. Such MAP readings, while potentially less accurate, are more convenient to gather because of the remote placement of the MAP connectors. Also, the modularity of the T-shaped tube allows the NCC device to be quickly configured to any desired use, either with or without a MAP measurement port.

Referring now to FIGS. 6 and 6A, NCC devices are shown with MAP connector embodiments which provide a pressure measurement closer to the nasal prongs 16, but which also have the MAP measurement port further away from the patient's face. FIG. 6 shows an NCC device embodiment 70' with a measurement port 52 angling off the bottom portion of the nasal prong section 14, as shown in FIG. 5. A MAP measurement tube 74 is connected to the port 52 and runs generally parallel to the supply tube 20. A T-shaped connector 76 allows the supply tube 20 to pass through the central portion of the connector 76, and routes the MAP measurement tube 74 out to a MAP measurement connector port 78.

Referring also to FIG. 6A, yet another NCC device embodiment 80 is shown with a nasal prong section 14, as similar to that shown in FIG. 1. In this embodiment, the supply tube 20 includes a branched off MAP measurement connection 82. The MAP measurement tube 84 extends from the supply tube 20 near the proximal end 85 of the supply tube where it connects with the nasal prong section 14. Tube 84 is flexible and generally parallels the supply tube 20, extending down away from the nose. The MAP measurement tube 84 ends in a MAP measurement connector port 86 for receiving a measurement probe. The port 86 is covered with a tethered cap or plug 87 when not in use.

In FIGS. 6 and 6A, the supply tube 20 is connected to a ventilator circuit attachment 12. The supply tube 20 might also be connected to a nasal cannula flow-meter connector 22 as shown in FIG. 1. Moreover, each addition or variation of the NCC device can be accomplished in a modular fashion, thereby allowing a user to take a variety of parts and construct a desired NCC device configuration.

Referring again FIGS. 5 and 6A, the MAP connector might also extend out from the supply tube 20 near the distal end of tube 20. A MAP measurement tube, similar to tube 84 in FIG. 6A, would be formed to extend along the interior of the supply tube 20 and would terminate near proximal end 85 to thereby take a measurement near the proximal end of the supply tube. This arrangement would provide the advantage of a proximal MAP measurement with a distal measurement connector, but without the tube 84 dangling to interfere with any other operations, procedures, and/or patient comfort.

The securement device, which adhesively attaches to the patient's upper lip and has tape strips for attaching the nasal cannula, could be used with device described above when configured as either a CPAP device, or a high flow nasal cannula. This unique securement device might also be used for other respiratory or gastric devices which would interact with the patient's nose and/or mouth. Such devices might include, for example, nasal-gastric tubes, PH probes, oral-gastric tubes, oral suction tubes, gastric secretions tubes, and/or conventional nasal cannulas.

It is to be understood that while a certain forms of the invention are illustrated, it is not to be limited to the specific forms or arrangements of parts herein described and shown. It will be apparent to those skilled in the art that various changes may be made without departing from the scope of the invention and the invention is not to be considered limited to what is shown in the drawings and descriptions.

What is claimed is:

1. A nasal CPAP cannula and securement apparatus comprising:
   a nasal prong section having a first and second gas inlet ends and a pair of nasal prong gas outlets in communication with said gas inlets disposed therebetween, said nasal prongs spaced apart for insertion into the nares of an individual;
   a pair of supply tubes with proximal and distal connector ends, each said proximal end connected to said first and second ends of said nasal prong section, and each said distal end of said supply tube having a connector means;
   a securement device having an arcuate securement strip of material with a plurality of adhesive tape strips extending therefrom wherein said arcuate securement strip is adhesively attached with an adhesive means to the individual's upper lip, and said nasal prong section is attached to said arcuate securement strip with said tape strips.

2. The nasal CPAP cannula securement apparatus of claim 1, wherein said apparatus includes a mean airway pressure (MAP) measurement port.

3. The nasal CPAP cannula and securement apparatus of claim 1, wherein said arcuate securement strip material is constructed of adhesive foam material and adhesive tape material.

4. The nasal CPAP cannula and securement apparatus of claim 1, wherein said arcuate securement strip curves upward and includes a first centered tape strip extending below said arcuate securement strip, and a second and third tape strip extending above said arcuate securement strip on either side of said nasal prongs of said nasal prong section, wherein said tape strips have a low tack adhesive and are covered with a removable adhesive surface covering.

5. The nasal CPAP cannula and securement apparatus of claim 4, wherein said arcuate securement strip has a top and bottom surface and includes a low tack adhesive with a removable covering on said bottom surface, said tape strip adhesive surfaces facing upward from said arcuate securement strip top surface, wherein said nasal prong section is positioned on said top surface of said arcuate securement strip and secured by said tape strips which are drawn around said nasal prong section and said arcuate securement strip.

6. The nasal CPAP cannula and securement apparatus of claim 1, wherein said nasal prong section includes a tab extending therefrom to assist in positioning said nasal prong section against said securement device.

7. The nasal CPAP cannula and securement apparatus of claim 1, wherein said supply tube distal ends are coupled to a ventilator circuit attachment means.

8. The nasal CPAP cannula and securement apparatus of claim 1, wherein said supply tube distal ends are coupled to a nasal cannula flow-meter attachment means.

9. The CPAP cannula and securement apparatus of claim 2, wherein said MAP measurement port is located on said nasal prong section.

10. The CPAP cannula and securement apparatus of claim 2, wherein said MAP measurement port is comprised of a flexible tube branching out from the side of one of said supply tubes.

11. The CPAP cannula and securement apparatus of claim 10, wherein said flexible tube branches out near said proximal end of said supply tube.

12. The CPAP cannula and securement apparatus of claim 10, wherein said flexible tube branches out near said distal end of said supply tube.

13. The CPAP cannula and securement apparatus of claim 10, wherein said flexible tube has an end connector with a tethered cap or plug.

14. The CPAP cannula and securement apparatus of claim 9, wherein said MAP measurement port has a flexible tube attached to said port and routed through a T-shaped sleeve which is positioned on said supply tube.

15. The CPAP cannula and securement apparatus of claim 2, wherein a T-shaped tubular fixture with a perpendicular juncture is connected to said distal end of one said supply tube, said juncture supplying said MAP measurement port.

16. The CPAP cannula and securement apparatus of claim 1, wherein said nasal prongs are conically shaped to facilitate a sealable fit with the nares.

17. A method of using said CPAP cannula and securement apparatus of claim 4, said method comprising the steps of:
   applying a skin adhesive to the upper lip of an individual;
   adhering said arcuate securement strip to said upper lip with the curvature of said arcuate securement strip pointing upwards;
   removing said peelably adhesive coverings from said tape strips;
   securing said nasal prong section in place with said nasal prongs positioned in the patient's nares by wrapping said second and third tape strips down over said nasal prong section outside said nasal prongs, and wrapping said first tape strip up over said nasal prong section between said nasal prongs.

18. The method of using said CPAP cannula and securement apparatus of claim 17, wherein said nasal prong section includes a positioning tab extending opposite said nasal prongs and said first tape strip is wrapped over said tab and said nasal prong section between said nasal prongs, said tab providing for gentle yet secure positioning of said nasal prongs against the patient's nose.

* * * * *